(12) United States Patent
Thornton, Jr.

(10) Patent No.: US 11,504,089 B2
(45) Date of Patent: Nov. 22, 2022

(54) SYSTEMS AND METHODS FOR MAKING FREQUENCY-BASED ADJUSTMENTS TO SIGNAL PATHS ALONG INTRAVASCULAR ULTRASOUND IMAGING SYSTEMS

(71) Applicant: Boston Scientific SciMed, Inc., Maple Grove, MN (US)

(72) Inventor: Peter Thornton, Jr., Los Altos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 348 days.

(21) Appl. No.: 16/141,602

(22) Filed: Sep. 25, 2018

(65) Prior Publication Data

US 2019/0090844 A1 Mar. 28, 2019

Related U.S. Application Data

(60) Provisional application No. 62/564,878, filed on Sep. 28, 2017.

(51) Int. Cl.
*A61B 8/00* (2006.01)
*A61B 8/12* (2006.01)
(Continued)

(52) U.S. Cl.
CPC ............ *A61B 8/445* (2013.01); *A61B 8/0891* (2013.01); *A61B 8/12* (2013.01); *A61B 8/4411* (2013.01);
(Continued)

(58) Field of Classification Search
CPC ....... A61B 8/0891; A61B 8/12; A61B 8/4411; A61B 8/445; A61B 8/4461; A61B 8/4494;
(Continued)

(56) References Cited

U.S. PATENT DOCUMENTS

| 4,841,977 A | 6/1989 | Griffith et al. |
| 5,375,602 A | 12/1994 | Lancee et al. |

(Continued)

FOREIGN PATENT DOCUMENTS

| EP | 2679167 | 1/2014 |
| EP | 2832295 | 2/2015 |

(Continued)

OTHER PUBLICATIONS

International Search Report and Written Opinion for PCT Application No. PCT/US2018/052685 dated Dec. 19, 2018.

*Primary Examiner* — Yi-Shan Yang
*Assistant Examiner* — Alexei Bykhovski
(74) *Attorney, Agent, or Firm* — Seager, Tufte & Wickhem, LLP

(57) ABSTRACT

An adaptor for adjusting electrical signals propagated along an electrically-conductive path between a drive unit and a catheter of an intravascular ultrasound imaging system includes a catheter connector disposed along a first end of a housing and configured to receive the catheter. A drive-unit connector is disposed along a second end of the housing and is configured to couple the adaptor to the drive unit. A catheter-conductor interface electrically-couples to a transducer conductor of the catheter. A drive-unit-conductor interface electrically-couples to an electrical conductor of the drive unit. An adaptor conductor electrically-couples the catheter-conductor interface to the drive-unit-conductor interface. A tuning element is electrically-coupled to the adaptor conductor and is configured to adjust electrical signals propagating along the adaptor conductor based, at least in part, on an operational frequency of a transducer disposed in the catheter.

15 Claims, 9 Drawing Sheets

(51) Int. Cl.
  *A61B 8/08* (2006.01)
  *G01S 15/89* (2006.01)
  *G01S 7/52* (2006.01)

(52) U.S. Cl.
  CPC .......... *A61B 8/4461* (2013.01); *A61B 8/4494* (2013.01); *A61B 8/461* (2013.01); *A61B 8/56* (2013.01); *G01S 7/52082* (2013.01); *G01S 15/894* (2013.01); *G01S 15/8956* (2013.01)

(58) Field of Classification Search
  CPC ......... A61B 8/461; A61B 8/56; G01S 15/894; G01S 15/8956; G01S 7/52082
  See application file for complete search history.

(56) References Cited

U.S. PATENT DOCUMENTS

| | | | |
|---|---|---|---|
| 5,643,297 A * | 7/1997 | Nordgren | ......... A61B 17/32075 604/22 |
| 6,945,938 B2 | 9/2005 | Grunwald | |
| 7,037,271 B2 | 5/2006 | Crowley | |
| 7,246,959 B2 | 7/2007 | Nakatani | |
| 7,306,561 B2 | 12/2007 | Sathyanarayana | |
| 7,622,853 B2 | 11/2009 | Rehrig et al. | |
| 8,523,778 B2 | 9/2013 | Sadaka | |
| 2004/0108789 A1 | 6/2004 | Marshall | |
| 2006/0058622 A1 | 3/2006 | Tearney et al. | |
| 2006/0084875 A1 | 4/2006 | Knight | |
| 2006/0100522 A1 | 5/2006 | Yuan et al. | |
| 2006/0106320 A1 | 5/2006 | Barbato | |
| 2006/0173350 A1 | 8/2006 | Yuan et al. | |
| 2006/0253028 A1 | 11/2006 | Lam et al. | |
| 2007/0016054 A1 | 1/2007 | Cao et al. | |
| 2007/0038111 A1 | 2/2007 | Rehrig et al. | |
| 2007/0083119 A1 | 4/2007 | Adachi et al. | |
| 2007/0167827 A1 * | 7/2007 | Masters | ................ A61B 8/12 600/463 |
| 2009/0163817 A1 | 6/2009 | Masters et al. | |
| 2009/0264769 A1 | 10/2009 | Sadaka | |
| 2010/0249603 A1 | 9/2010 | Hastings et al. | |
| 2011/0071400 A1 | 3/2011 | Hastings et al. | |
| 2011/0098573 A1 | 4/2011 | Thornton et al. | |
| 2011/0207995 A1 | 8/2011 | Snow et al. | |
| 2012/0197113 A1 * | 8/2012 | Courtney | ............ G10K 11/352 600/427 |
| 2012/0253197 A1 | 10/2012 | Sadaka | |
| 2013/0079642 A1 | 3/2013 | Marshall et al. | |
| 2013/0216114 A1 * | 8/2013 | Courtney | ................ A61B 8/12 382/130 |
| 2015/0196285 A1 * | 7/2015 | Mori | ................... A61B 5/0035 600/427 |
| 2015/0359510 A1 * | 12/2015 | Currlin | ................... A61B 8/12 600/467 |
| 2018/0280680 A1 * | 10/2018 | Isaacson | ................ A61N 7/00 |

FOREIGN PATENT DOCUMENTS

| | | |
|---|---|---|
| JP | 2005177205 | 7/2005 |
| JP | 20110152274 | 8/2011 |
| WO | 2009/048339 | 4/2009 |
| WO | 2009/073752 | 6/2009 |
| WO | 2009/121067 | 10/2009 |

* cited by examiner

SYSTEMS AND METHODS FOR MAKING FREQUENCY-BASED ADJUSTMENTS TO SIGNAL PATHS ALONG INTRAVASCULAR ULTRASOUND IMAGING SYSTEMS

CROSS-REFERENCE TO RELATED APPLICATIONS

This application claims the benefit under 35 U.S.C. § 119(e) of U.S. Provisional Patent Application Ser. No. 62/564,878, filed Sep. 28, 2017, which is incorporated herein by reference.

TECHNICAL FIELD

The present invention is directed to the area of intravascular ultrasound imaging systems and methods of making and using the systems. The present invention is also directed to intravascular ultrasound imaging systems that include adaptors for adjusting signal paths within the systems based, at least in part, on operational frequencies of catheters, as well as methods for making and using the adaptors, catheters, and systems.

BACKGROUND

Intravascular ultrasound ("IVUS") imaging systems have proven diagnostic capabilities for a variety of diseases and disorders. For example, IVUS imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety of diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic signals that are transmitted through patient tissue. Reflected pulses of the transmitted acoustic signals are absorbed by the one or more transducers and transformed to electric pulses. The transformed electric pulses are delivered to the image processor and converted to an image displayable on the monitor.

BRIEF SUMMARY

In one embodiment, an adaptor for adjusting electrical signals propagated along an electrically conductive path between a drive unit and a catheter of an intravascular ultrasound imaging system includes a housing having a first end and a second end. A catheter connector is disposed along the first end of the housing and is configured to receive the catheter. A drive-unit connector is disposed along the second end of the housing and is configured to couple the adaptor to the drive unit. A catheter-conductor interface is disposed along the first end of the housing and is configured to electrically couple to a transducer conductor extending along the catheter. A drive-unit-conductor interface is disposed along the second end of the housing and is configured to electrically couple to an electrical conductor of the drive unit. An adaptor conductor electrically couples the catheter-conductor interface to the drive-unit-conductor interface. A tuning element is electrically coupled to the adaptor conductor. The tuning element is configured to adjust electrical signals propagating along the at least one adaptor conductor based, at least in part, on an operational frequency of a transducer disposed in the catheter.

In at least some embodiments, the adaptor further includes a rotatable shaft disposed in the housing and extending from the catheter connector to the drive-unit connector. The rotatable shaft is configured to transfer rotational motion generated within the drive unit to a drive cable or driveshaft within the catheter when the catheter is received by the catheter connector and the adaptor is coupled to the drive unit. In at least some embodiments, the at least one tuning element is disposed entirely within the rotatable shaft.

In at least some embodiments, the adaptor further includes a rotary transformer disposed in the housing. In at least some embodiments, the adaptor further includes a transmitter/receiver disposed in the housing. In at least some embodiments, the adaptor further includes a catheter release disposed along the housing, the catheter release configured and arranged to enable a user to manually separate the catheter from the adaptor when the catheter is received by the catheter connector.

In at least some embodiments, the at least one tuning element comprises at least one filter. In at least some embodiments, the at least one tuning element comprises at least one common mode choke. In at least some embodiments, the at least one tuning element comprises at least one tuning circuit. In at least some embodiments, the at least one tuning element is configured and arranged to adjust signals propagated along the at least one adaptor conductor to reduce noise in images generated from the intravascular ultrasound imaging system.

In at least some embodiments, the at least one tuning element is configured and arranged to adjust electrical signals propagating along the at least one adaptor conductor when those electrical signals correspond to an operational frequency of the at least one transducer of the catheter that is within a first frequency range. In at least some embodiments, the first frequency range is no less than 5 MHz and no greater than 65 MHz. In at least some embodiments, the first frequency range is no less than 5 MHz and no greater than 35 MHz. In at least some embodiments, the first frequency range is no less than 35 MHz and no greater than 65 MHz.

In another embodiment, a catheter assembly for an intravascular ultrasound system includes a catheter having a longitudinal length, a distal portion, and a proximal portion. The catheter defines a lumen extending along at least a portion of the catheter. An imaging device housing is disposed in the lumen along the distal portion of the catheter. At least one ultrasound transducer is disposed in the imaging device housing. The at least one ultrasound transducer is configured to transform applied electrical signals to acoustic signals within a frequency bandwidth centered at an operational frequency, transmit the acoustic signals, receive corresponding echo signals, and transform the received echo signals to electrical signals. At least one transducer conductor is electrically coupled to the at least one transducer and is in electrical communication with the proximal end of the catheter. The above-described adapter is coupleable to the proximal portion of the catheter.

In yet another embodiment, a method for imaging a patient using an intravascular ultrasound imaging system includes providing the catheter assembly described above. The adaptor of the catheter assembly is coupled to a drive unit. The proximal portion of the catheter of the catheter assembly is coupled to the adaptor. The distal portion of the catheter is inserted into patient vasculature. Patient tissue is imaged using at least one transducer disposed in the catheter while the catheter is inserted into the patient vasculature. Electrical signals propagating between the drive unit and the at least one transducer are adjusted using at least one tuning element disposed in the adaptor based, at least in part, on the operational frequency of the at least one transducer. Images generated while imaging the patient tissue using the at least one transducer are displayed.

In at least some embodiments, providing the catheter assembly includes selecting a catheter having a first operational frequency; and selecting an adaptor configured for adjusting electrical signals propagating between the drive unit and the at least one transducer when those electrical signals correspond to operation of the at least one transducer within a first frequency range that includes the first operational frequency of the catheter.

In at least some embodiments, selecting an adaptor includes selecting an adaptor configured for adjusting electrical signals corresponding to operation of the at least one transducer within a first frequency range that is no less than 5 MHz and no greater than 65 MHz.

In at least some embodiments, selecting an adaptor includes selecting an adaptor configured for adjusting electrical signals corresponding to operation of the at least one transducer within a first frequency range that is no less than 5 MHz and no greater than 35 MHz.

In at least some embodiments, selecting an adaptor includes selecting an adaptor configured for adjusting electrical signals corresponding to operation of the at least one transducer within a first frequency range that is no less than 35 MHz and no greater than 65 MHz.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of intravascular ultrasound imaging systems and methods of making and using the systems. The present invention is also directed to intravascular ultrasound imaging systems that include adaptors for adjusting signal paths within the systems based, at least in part, on operational frequencies of catheters, as well as methods for making and using the adaptors, catheters, and systems.

Suitable intravascular ultrasound ("IVUS") imaging systems include, but are not limited to, one or more transducers disposed on a distal portion of a catheter configured and arranged for percutaneous insertion into a patient. Examples of IVUS imaging systems with catheters are found in, for example, U.S. Pat. Nos. 7,306,561; and 6,945,938; as well as U.S. Patent Application Publication Nos. 20060253028; 20070016054; 20070038111; 20060173350; and 20060100522, all of which are incorporated by reference.

Figure 1:
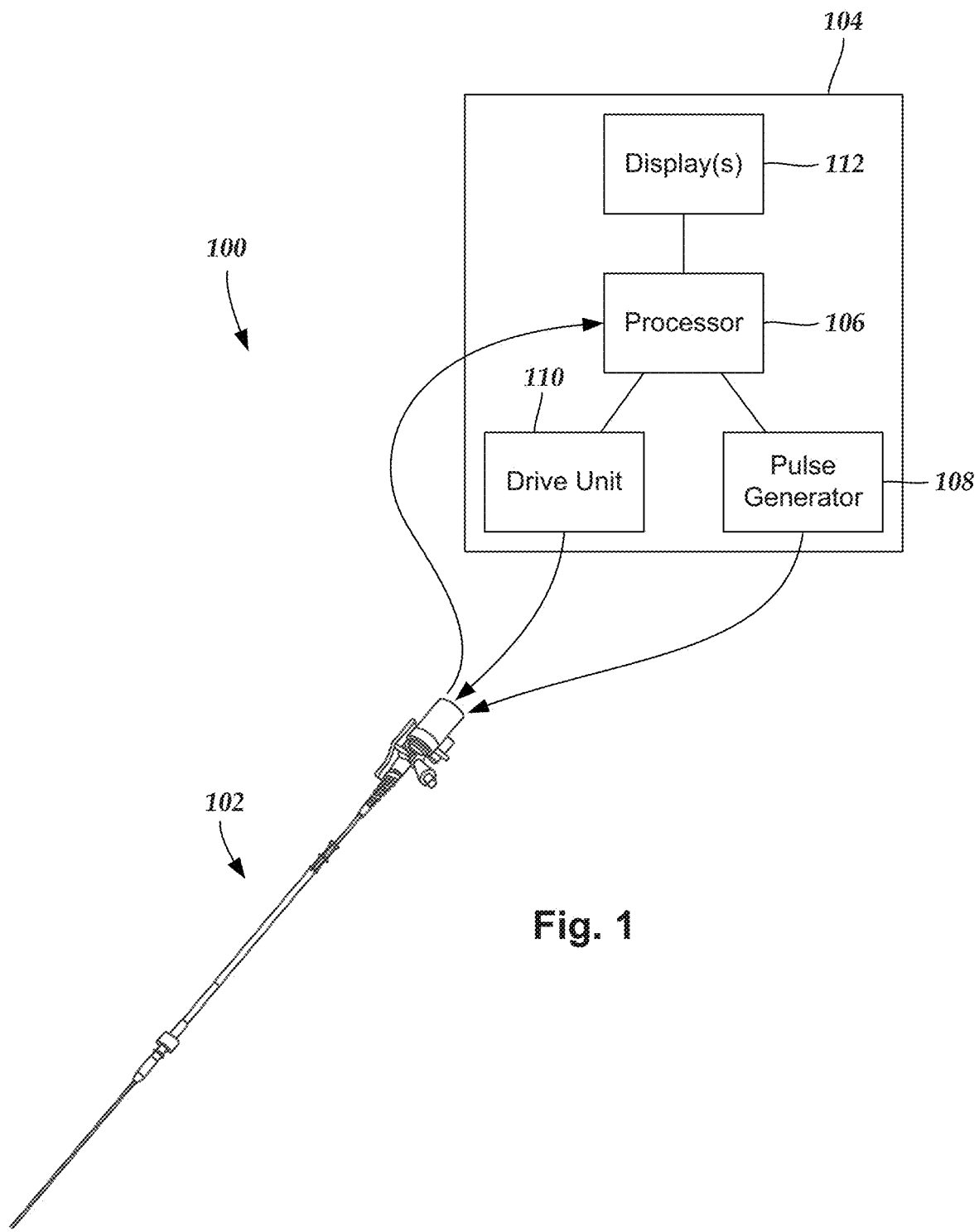
FIG. 1 is a schematic view of one embodiment of an intravascular ultrasound imaging system, according to the invention.

FIG. 1 schematically shows one embodiment of an IVUS imaging system 100. The IVUS imaging system 100 includes a catheter 102 that is coupleable to a control module 104. The control module 104 may include, for example, a processor 106, a pulse generator 108, a drive unit 110, and one or more displays 112. In at least some embodiments, the pulse generator 108 forms electric signals that are input to one or more transducers (312 in FIG. 3) disposed in the catheter 102. In at least some embodiments, electric signals transmitted from the one or more transducers (312 in FIG. 3) is input to the processor 106 for processing. The processed electric signals from the one or more transducers (312 in FIG. 3) may be displayed as one or more images on the one or more displays 112. In at least some embodiments, mechanical energy from the drive unit 110 is used to drive an imaging core (306 in FIG. 3) disposed in the catheter 102.

The processor 106 may also be used to control the functioning of one or more of the other components of the control module 104. For example, the processor 106 may be used to control at least one of the frequency or duration of the electrical signals transmitted from the pulse generator 108, the rotation rate of the imaging core (306 in FIG. 3) by the drive unit 110, the velocity or length of the pullback of the imaging core (306 in FIG. 3) by the drive unit 110, or one or more properties of one or more images formed on the one or more displays 112.

Figure 2:
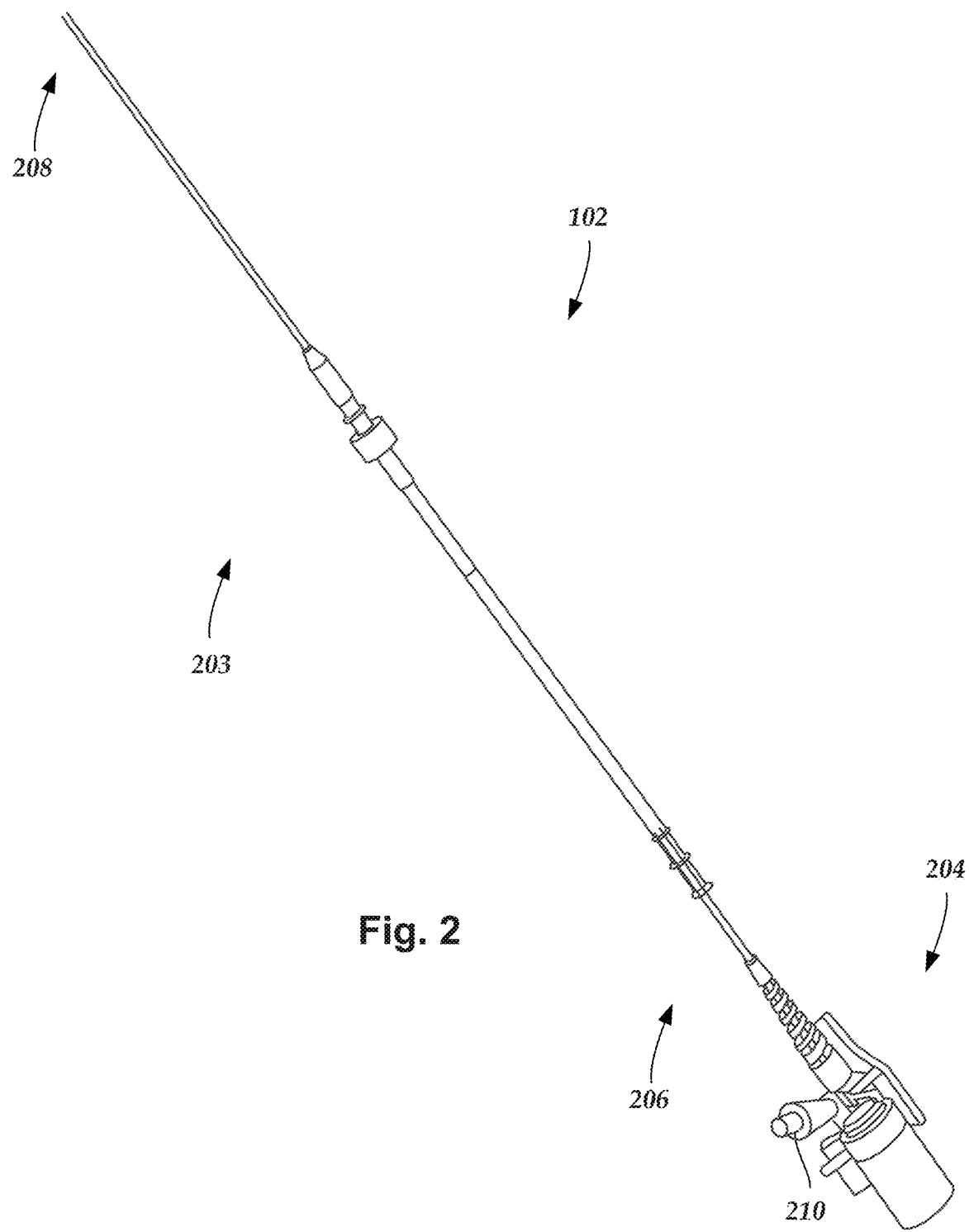
FIG. 2 is a schematic side view of one embodiment of a catheter of an intravascular ultrasound imaging system, according to the invention.

FIG. 2 shows, in schematic side view, one embodiment of the catheter 102 of the IVUS imaging system (100 in FIG. 1). The catheter 102 includes an elongated member 203 and a hub 204. The elongated member 203 includes a proximal portion 206 and a distal portion 208. In FIG. 2, the proximal portion 206 of the elongated member 203 is coupled to the catheter hub 204 and the distal portion 208 of the elongated member is configured and arranged for percutaneous insertion into a patient. In at least some embodiments, the catheter 102 defines at least one flush port, such as flush port 210. In at least some embodiments, the flush port 210 is defined in the hub 204. In at least some embodiments, the hub 204 is configured and arranged to couple to the control module (104 in FIG. 1). In some embodiments, the elongated member 203 and the hub 204 are formed as a unitary body. In other embodiments, the elongated member 203 and the hub 204 are formed separately and subsequently assembled together.

Figure 3:
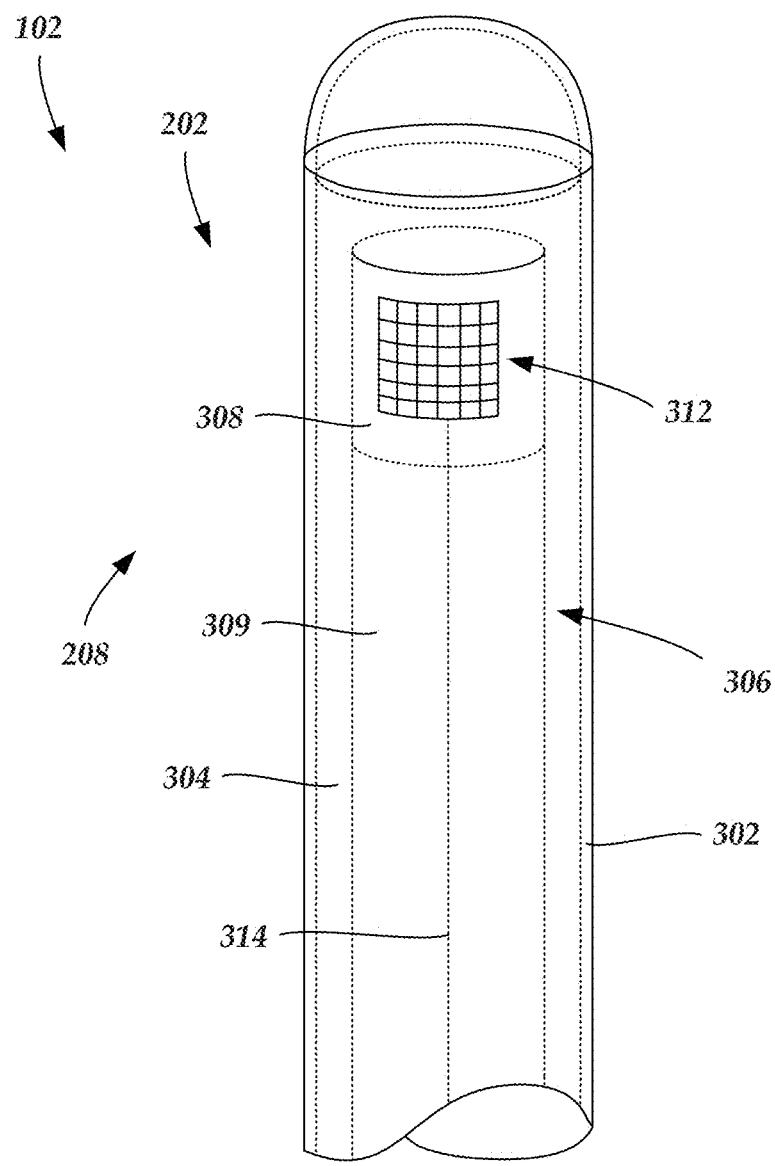
FIG. 3 is a schematic perspective view of one embodiment of a distal end of the catheter shown in FIG. 2 with an imaging core disposed in a lumen defined in the catheter, according to the invention.

FIG. 3 shows, in schematic perspective view, one embodiment of the distal portion 208 of the elongated member 203 of the catheter 102. The elongated member 203 includes a sheath 302 and a lumen 304. An imaging core 306 is disposed in the lumen 304. The imaging core 306 includes an imaging device housing 308 coupled to a distal end of a transducer connection system, such as a drive cable or driveshaft 309.

The sheath 302 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

One or more transducers 312 may be mounted to the imaging device housing 308 and employed to transmit and receive acoustic signals. In a preferred embodiment (as shown in FIG. 3), an array of transducers 312 are mounted to the imaging device housing 308. In other embodiments, a single transducer may be employed. In yet other embodiments, multiple transducers in an irregular-array may be employed. Any number of transducers 312 can be used. For example, there can be one, two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used.

The one or more transducers 312 may be formed from one or more known materials capable of transforming applied electrical signals to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like.

The pressure distortions on the surface of the one or more transducers 312 form acoustic signals of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic signals of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 312 may include a layer of piezoelectric material sandwiched between a conductive acoustic lens and a conductive backing material formed from an acoustically absorbent material (e.g., an epoxy substrate with tungsten particles). During operation, the piezoelectric layer may be electrically excited by both the backing material and the acoustic lens to cause the emission of acoustic signals.

In at least some embodiments, the one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form an image of the walls of the blood vessel and tissue surrounding the blood vessel.

In at least some embodiments, the imaging core 306 is rotated about a longitudinal axis of the catheter 102. As the imaging core 306 rotates, the one or more transducers 312 emit acoustic signals in different radial directions. When an emitted acoustic signal with sufficient energy encounters one or more medium boundaries, such as one or more tissue boundaries, a portion of the emitted acoustic signal is reflected back to the emitting transducer as an echo signal. Each echo signal that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic signals transmitted and the echo signals received. In at least some embodiments, the rotation of the imaging core 306 is driven by the drive unit 110 disposed in the control module (104 in FIG. 1) via the transducer connection system 309.

As the one or more transducers 312 rotate about the longitudinal axis of the catheter 102 emitting acoustic signals, multiple images are formed that collectively form a radial cross-sectional image of a portion of the region surrounding the one or more transducers 312, such as the walls of a blood vessel of interest and the tissue surrounding the blood vessel. In at least some embodiments, the radial cross-sectional image can be displayed on one or more displays 112.

In at least some embodiments, the imaging core 306 may also move axially along the blood vessel within which the catheter 102 is inserted so that a plurality of cross-sectional images may be formed along an axial length of the blood vessel. In at least some embodiments, during an imaging procedure the one or more transducers 312 are retracted (i.e., pulled back) along the longitudinal length of the catheter 102. In at least some embodiments, the catheter 102 includes at least one telescoping section that can be retracted during pullback of the one or more transducers 312. In at least some embodiments, the drive unit 110 drives the pullback of the imaging core 306 within the catheter 102. In at least some embodiments, the drive unit 110 pullback distance of the imaging core is at least 5 cm. In at least some embodiments, the drive unit 110 pullback distance of the imaging core is at least 10 cm. In at least some embodiments, the drive unit 110 pullback distance of the imaging core is at least 15 cm. In at least some embodiments, the drive unit 110 pullback distance of the imaging core is at least 20 cm. In at least some embodiments, the drive unit 110 pullback distance of the imaging core is at least 25 cm.

The quality of an image produced at different depths from the one or more transducers 312 may be affected by one or more factors including, for example, bandwidth, transducer focus, beam pattern, as well as the frequency of the acoustic signal. The frequency of the acoustic signal output from the one or more transducers 312 may also affect the penetration depth of the acoustic signal output from the one or more transducers 312. In general, as the frequency of an acoustic signal is lowered, the depth of the penetration of the acoustic signal within patient tissue increases. In at least some embodiments, the IVUS imaging system 100 transmits acoustic signals centered at an operational frequency. The operational frequency is typically within a range of 5 MHz to 60 MHz. The acoustic signals may be transmitted within a frequency bandwidth that includes the operational frequency.

In at least some embodiments, the one or more transducers 312 may be mounted to the distal portion 208 of the imaging core 306. The imaging core 306 may be inserted in the lumen of the catheter 102. In at least some embodiments, the catheter 102 (and imaging core 306) are inserted percutaneously into a patient via an accessible blood vessel, such as the femoral artery, at a site remote from a target imaging location. The catheter 102 may then be advanced through patient vasculature to the target imaging location, such as a portion of a selected blood vessel.

As discussed above, the transducer connection system 309 couples the imaging device housing 308 to the control module (104 in FIG. 1). In at least some embodiments, the one or more transducer conductors 314 extend along the transducer connection system 309. In at least some embodiments, one or more transducer conductors 314 electrically couple the one or more transducers 312 to the control module 104 (104 in FIG. 1).

In designing a transducer connection system that utilizes a drive cable, it is useful to consider the torsional stiffness of the drive cable. The drive cable is formed to be torsionally stiff ("stiff") enough to carry a torque sufficient to rotate the one or more transducers at the distal end of the imaging core, yet flexible enough to maneuver the one or more transducers through potentially tortuous patient vasculature to target imaging locations. It is undesirable for the drive cable to experience substantial "wind up" which occurs as a result of twisting along a length of the drive cable.

Moreover, it is desirable to have sufficient torque to maintain uniform rotation of the imaging core 306 during operation. For example, when the imaging core 306 is pulled back during an imaging procedure, it is desirable for the imaging core 306 to be able to maneuver through tortuous or narrow regions which may press against one or more portions of the imaging core 306 within the catheter 102 without causing a non-uniform rotation (e.g., a wobble, a vibration, a stall, or the like) of the one or more transducers 312 during operation. Non-uniform rotation may lead to the distortion of a subsequently-generated IVUS image (e.g., the subsequently-generated IVUS image may include distortions, spurious details or features, or the like or combinations thereof).

Figure 4:
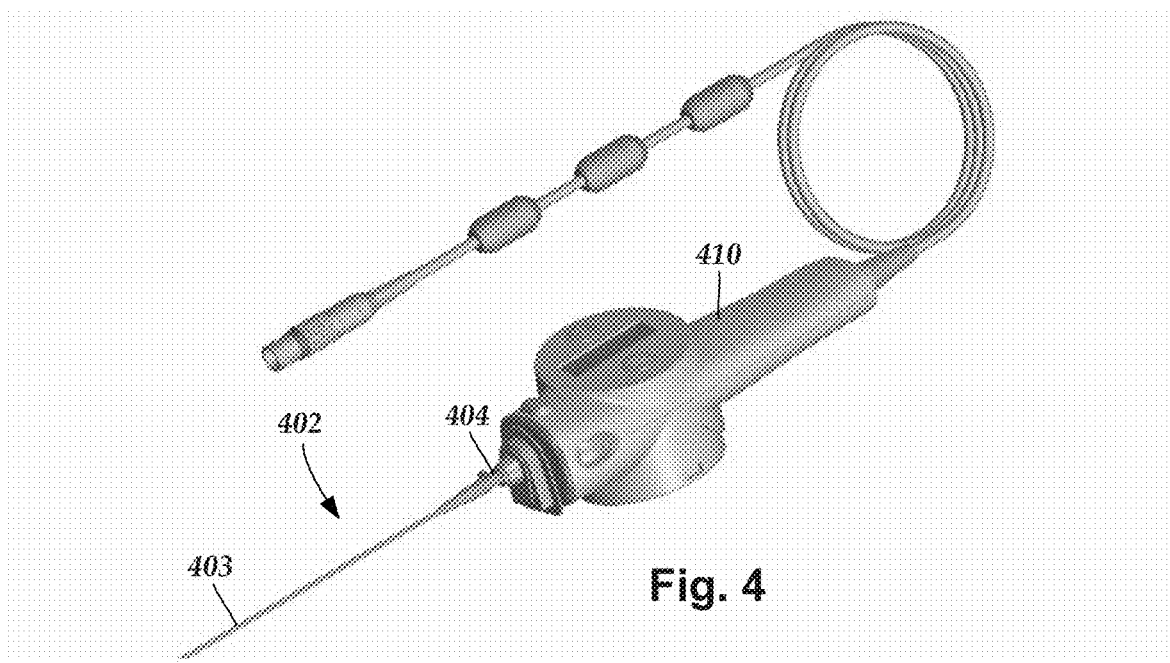
FIG. 4 is a schematic perspective view of one embodiment of a catheter coupled to a drive unit of an intravascular ultrasound imaging system, according to the invention.

FIG. 4 shows, in perspective view, one embodiment of a catheter 402 coupled to a drive unit 410. The catheter 402 includes an elongated member 403 and a hub 404. As shown in FIG. 4, the hub 404 of the catheter 402 is coupled to the drive unit 410 with the elongated member 403 extending outward from the drive unit 410. As described above, the drive unit 410 can be coupled to one or more other components of an IVUS imaging system, such as a pulse generator, a processor, a display, or the like.

Figure 5A:
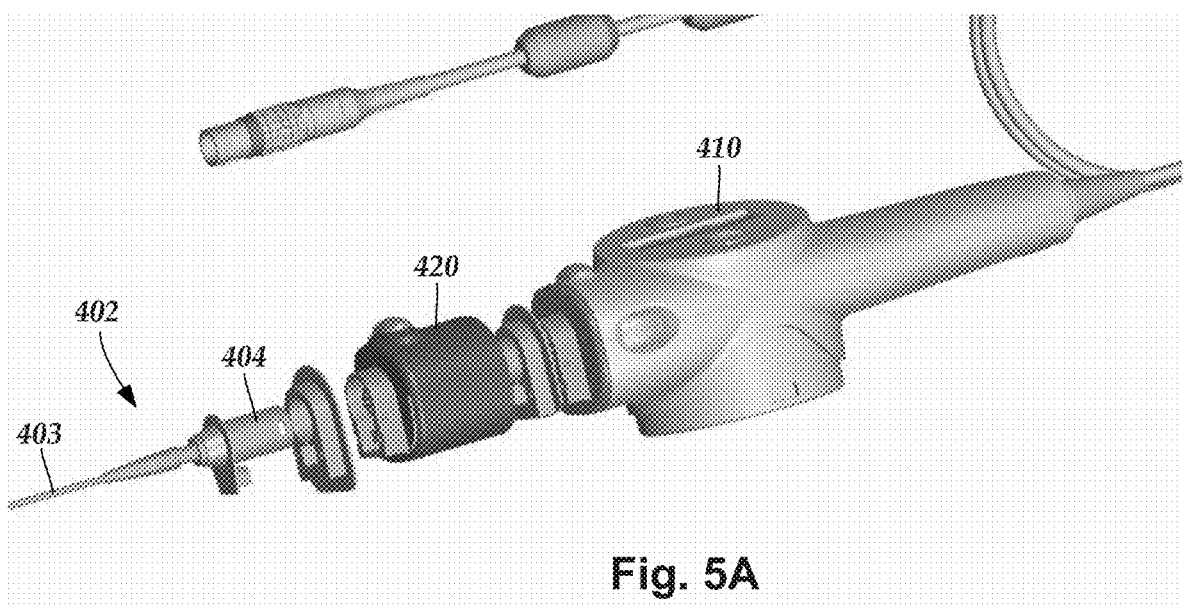
FIG. 5A is a schematic perspective, exploded view of one embodiment of the catheter of FIG. 4 coupleable to the drive unit of FIG. 4 via an adaptor, according to the invention.

Turning to FIG. 5A, drive units are typically reusable and are compatible with a variety of different catheters. The different catheters that are compatible with a drive unit may house transducers having different operational frequencies at which the transducers operate. For example, a first catheter coupleable with the drive unit may house one or more transducers having operational frequencies of 60 MHz, while a second catheter coupleable with the same drive unit may house one or more transducers having operational frequencies of 9 MHz.

In at least some instances, the drive unit has an established frequency response that cannot change. The drive unit may include components (e.g., a transmitter, receiver, rotary transformer, and the like) along the signal path that are insufficient to operate consistently across a wide range of catheter frequencies (e.g., 9 MHz to 60 MHz). For example, a transmitter may generate a sinusoidal pulse at some frequencies and a square wave at other frequencies, thereby potentially increasing the numbers and strengths of harmonic signals. As another example, a transformer may have a center frequency of approximately 30 MHz, where the transformer rolls off significantly at higher frequencies and precipitously below 10 MHz.

Accordingly, a particular drive unit may, for example, function well with catheters having an operational frequency of 60 MHz, but may not function as well with catheters having an operational frequency of 9 MHz, or vice versa. Consequently, it may be the case that catheters with certain operational frequencies suffer from reduced functionality including, for example, excess noise, poor image quality, excess emissions, low sensitivity, distortions, spurious features, or the like, while catheters with other operational frequencies function comparatively well.

One option for dealing with this problem is to use different drive units for catheters with different operational frequencies, where each different drive unit is adapted for use with a particular operational frequency, or range of operational frequencies. Drive units, however, can be expensive. And using different drive units for catheters with different operational frequencies can be confusing, laborious, and time-consuming. Another option is to position tuning elements along catheters, where the tuning elements are configured to enhance performance of the IVUS imaging system at the particular operational frequencies of the catheters. Catheters, however, may be inadequately-sized to accommodate the tuning elements needed to enhance performance. Additionally, the costs associated with incorporating tuning elements into each catheter may be cost-preventative.

As herein described, an adaptor is useful for enhancing performance of an IVUS imaging system when used with one or more corresponding catheters. The adaptor is coupleable between a catheter and a drive unit. In at least some embodiments, the adaptor is coupleable between the catheter hub and the drive unit. In at least some embodiments, the adaptor is reusable.

The adaptor is configured to adjust the signal path between the drive unit and the catheter to enhance performance along one or more ranges of transducer frequencies corresponding to the operational frequency of the catheter. The adaptor thereby enables use of a wide range of different transducer frequencies, to improve image quality, without sacrificing potential ill-effects along the signal path between the catheter and the drive unit caused by inconsistent functionality of the drive unit with at least some frequencies within the wide range of transducer frequencies used by different catheters.

Figure 5B:
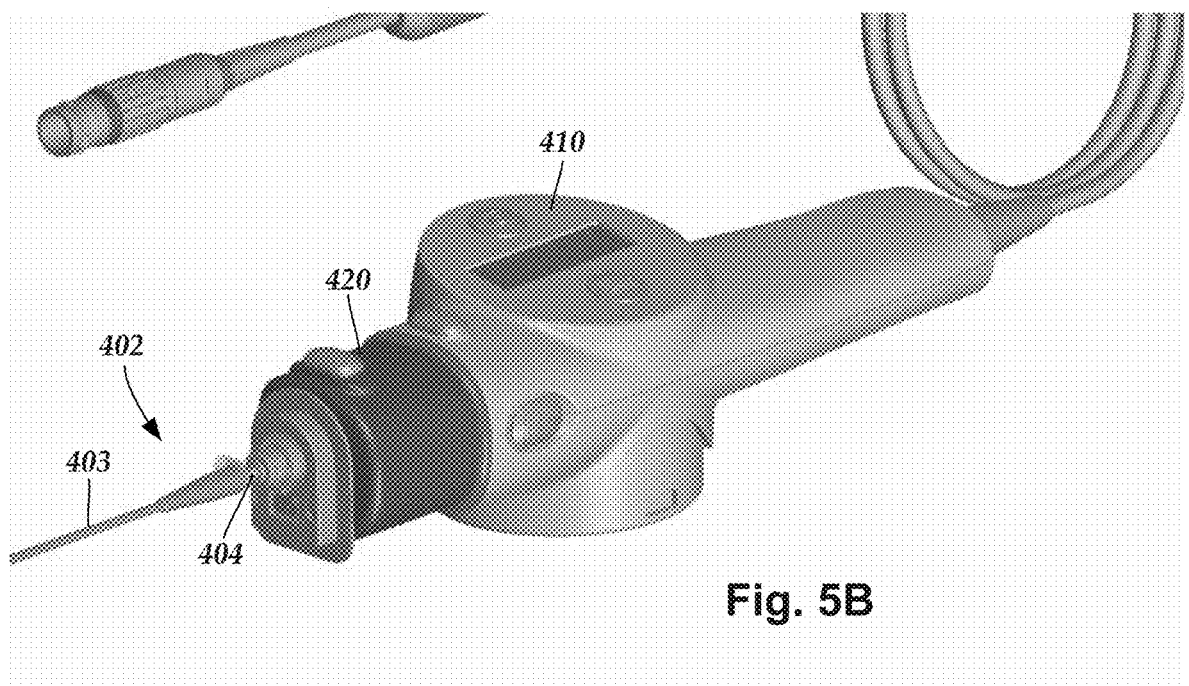
FIG. 5B is a schematic perspective view of one embodiment of the catheter of FIG. 4 coupled to the drive unit of FIG. 4 via an adaptor, according to the invention.

FIG. 5A shows, in perspective, exploded view, the catheter 402, the drive unit 410, and an adaptor 420 positioned between the catheter 402 and the drive unit 410. FIG. 5B shows, in perspective view, the adaptor 420 coupled to each of the catheter 402 and the drive unit 410. As shown in FIGS. 5A-5B, in at least some embodiments the adaptor 420 is configured to receive the catheter hub 404 and the drive unit 410 along opposing ends.

The adaptor includes tuning elements configured for enhancing performance of an IVUS imaging system when used with catheters having operational frequencies of a particular frequency, or range of frequencies. Accordingly, a single drive unit can be used with a variety of different catheters having a range of different operational frequencies without sacrificing performance along at least some of those operational frequencies and without needing to dispose tuning elements within each catheter.

In at least some embodiments, the tuning elements enhance performance by reducing noise, improving image quality, reduce emissions, improving sensitivity, or the like or combinations thereof. In at least some embodiments, the tuning elements filter out unwanted spurious resonances of a transducer as a result of the harmonics. Adding the tuning elements can, in some instances, reduce the resonances outside of the useful frequency range. Such a reduction of spurious resonances can reduce the signal-to-noise ratio and increase excitation voltage on the transducer for improving imaging.

In some embodiments, the adaptor is configured to enhance performance of IVUS imaging systems with fully functional catheters and fully functional drive units. In other words, were the catheter to be coupled directly into the drive unit (i.e., without the adaptor therebetween), the system would still be functional to produce one or more IVUS images.

Figure 6:
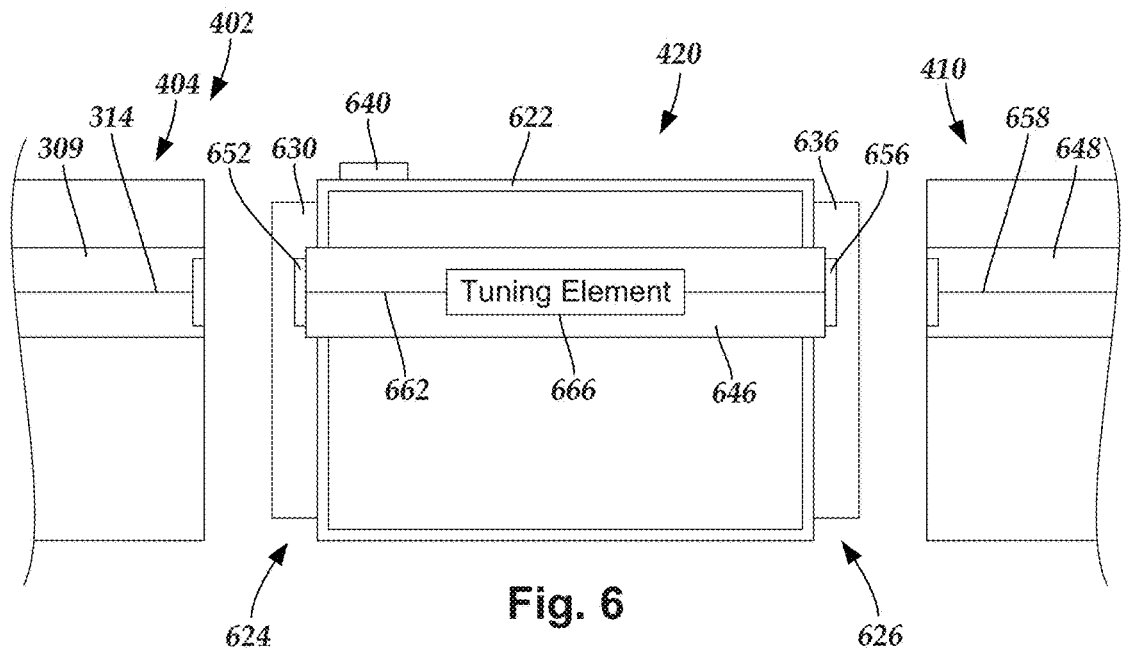
FIG. 6 is a schematic side view of one embodiment of the adaptor of FIG. 5 disposed between the catheter of FIG. 4 and the drive unit of FIG. 4, according to the invention.
Figure 7A:
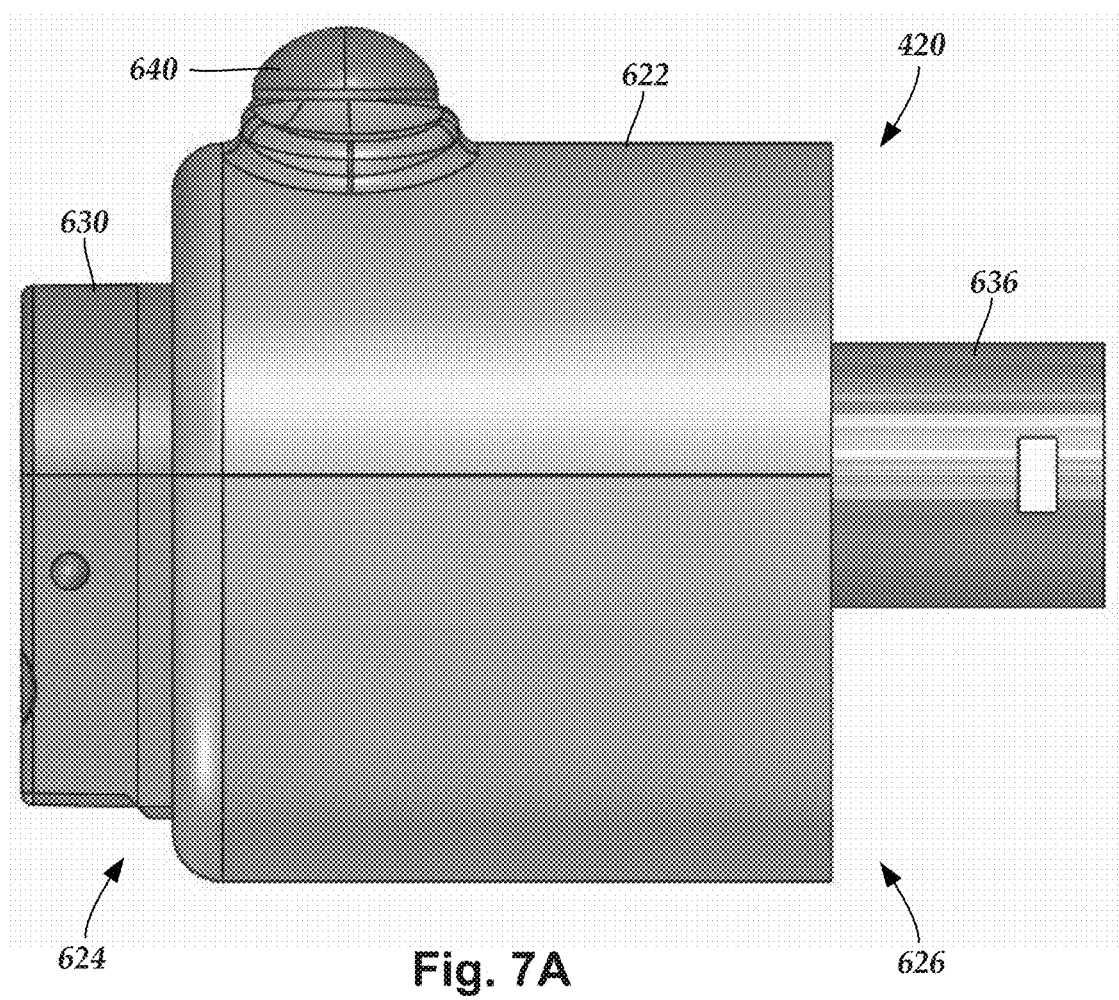
FIG. 7A is a schematic side view of one embodiment of the adaptor of FIG. 5, according to the invention.
Figure 7B:
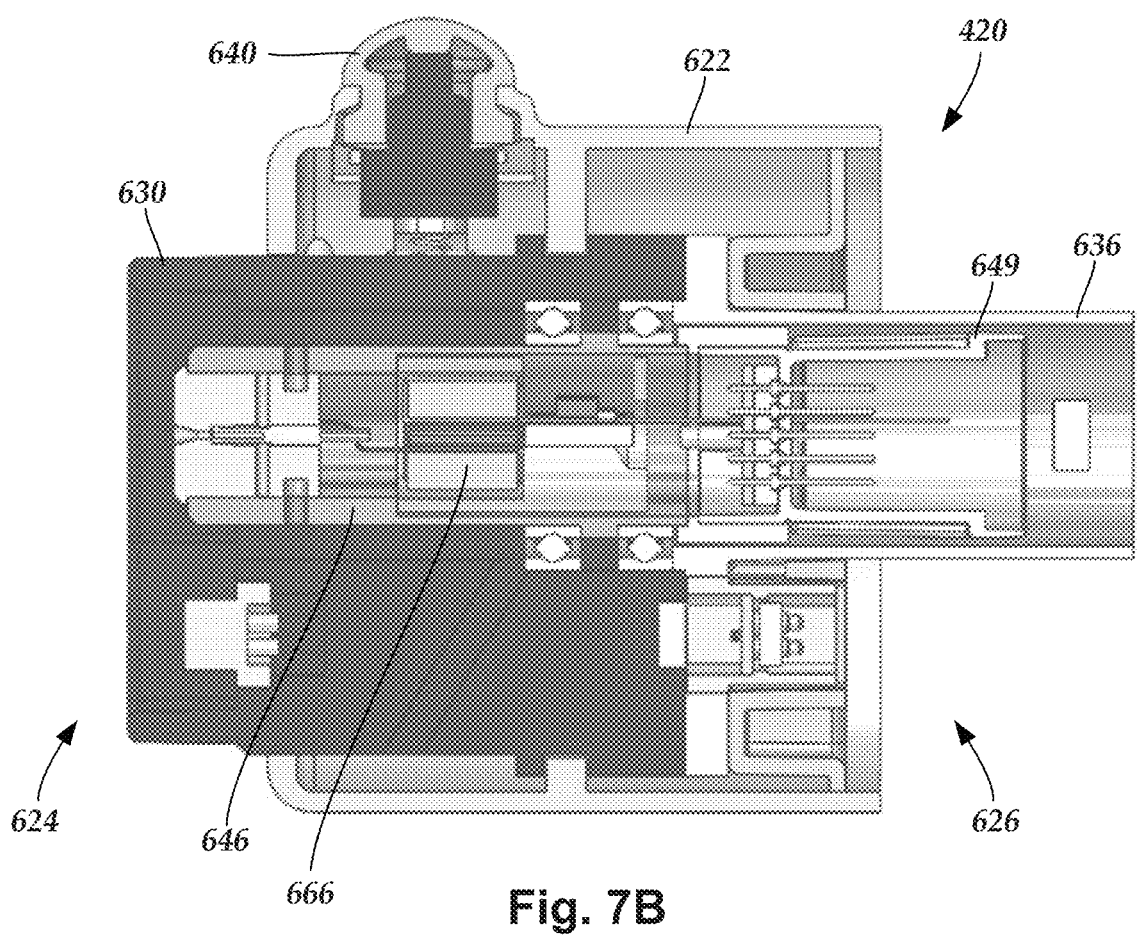
FIG. 7B is a schematic cross-sectional view of one embodiment of the adaptor of FIG. 7A, according to the invention.
Figure 8:
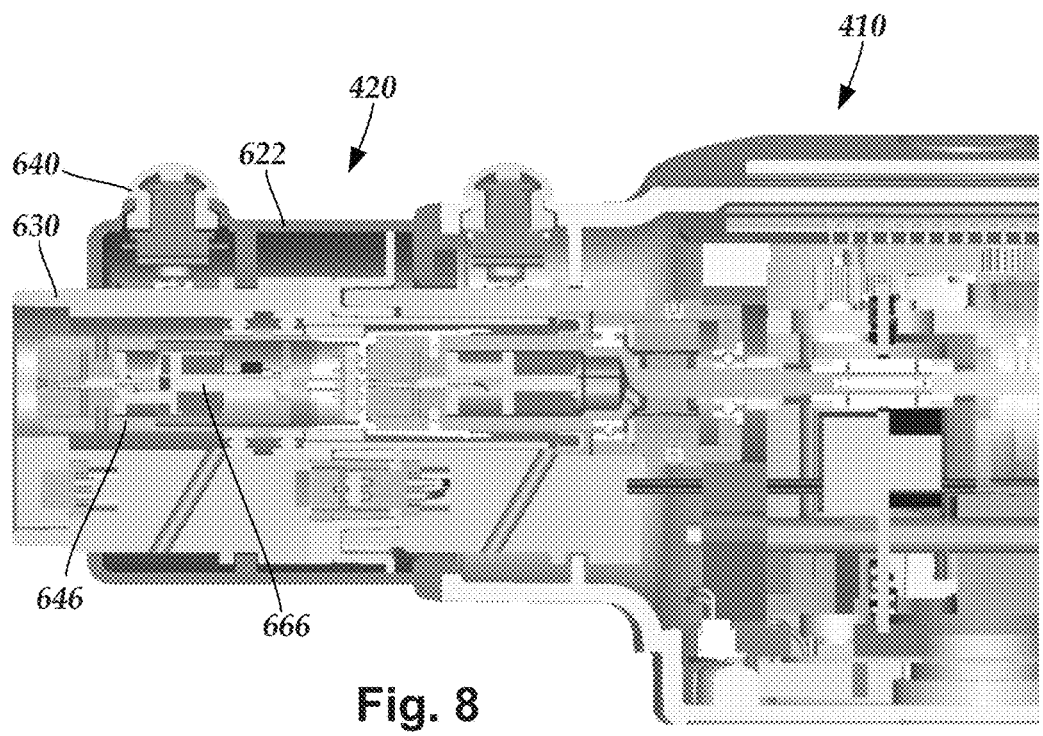
FIG. 8 is a schematic cross-sectional view of one embodiment of the adaptor of FIGS. 7A-7B coupled to the drive unit of FIG. 4, according to the invention.

FIG. 6 shows, in schematic side view, one embodiment of the adaptor 420 positioned between the catheter 402 and the drive unit 410. FIG. 7A shows, in side view, one embodiment of the adaptor 420. FIG. 7B shows, in cross-sectional view, one embodiment of the adaptor 420. FIG. 8 shows, in cross-sectional view, one embodiment of the adaptor 420 coupled to the drive unit 410.

The adaptor 420 includes a housing 622 having a first end 624 and a second end 626. In at least some embodiments, the second end 626 is opposite to the first end 624. A catheter connector 630 is disposed along the first end 624 of the housing 622 and is configured for receiving a proximal end of a catheter, such as the hub 404 of the catheter 402. In at least some embodiments, the catheter connector 630 is similar to a catheter-receiving connector of a conventional drive unit. In at least some embodiments, the catheter connector 630 is configured for receiving a catheter hub by plugging the catheter hub into the catheter connector 630.

A drive-unit connector 636 is disposed along the second end 626 of the housing 622 and is configured for coupling the adaptor 420 to the drive unit 410. In at least some embodiments, the drive-unit connector 636 is similar to a drive-unit-receiving connector of a conventional catheter hub. In at least some embodiments, the drive-unit connector 636 plugs into the drive unit 410.

In FIG. 6, the catheter connector 630 and the drive-unit connector 636 are both shown extending outwardly from the housing 622, for clarity of illustration. In at least some embodiments (and as shown in FIGS. 7A-8), at least a portion of at least one of the catheter connector 639 or the drive-unit connector 636 extends inwardly with respect to the housing 622.

An optional catheter release 640 is disposed along the housing 622. The catheter release 640 controls release of the catheter 402 from the adaptor 420 when the catheter 402 is coupled to the adaptor 420. In at least some embodiments, once the catheter 402 is received by the adaptor 420, the catheter 402 remains retained by the adaptor 420 until the catheter release 640 is activated to enable the catheter 402 to be removed from the adaptor 420. In at least some embodiments, the catheter release 640 is configured to enable a user to manually separate the catheter 402 from the adaptor 420 when the catheter is received by the catheter connector 630.

The adaptor 420 includes a rotatable shaft 646 disposed in the housing 622. The rotatable shaft 646 is suitable for transferring rotation generated by the drive unit 410 (e.g., by a drive-unit driveshaft 648) to the drive cable or driveshaft 309 of the catheter 402. In at least some embodiments, the rotatable shaft 646 extends from the catheter connector 630 to a drive-shaft coupler disposed along, or in proximity to, the second end 626 of the housing 622.

The adaptor 420 also is configured to enable one or more electrical signal paths to extend between the drive unit and the catheter. The adaptor 420 includes a catheter conductor interface 652 disposed along the first end 624 of the housing 622 and configured to electrically couple to at least one transducer conductor 309 extending along the catheter 402. Similarly, a drive-unit conductor interface 656 is disposed along the second end 626 of the housing 622 and is configured to electrically couple to at least one electrical conductor 658 of the drive unit 410. The catheter conductor interface 652, or the drive-unit conductor interface 656, or both, can be formed in any suitable manner, such as pin headers.

In FIG. 6, the catheter conductor interface 652 is shown disposed along the catheter connector 630 within the rotatable shaft 646. It will be understood that the catheter conductor interface 652 can be disposed at any suitable location along the catheter connector 630, either within, or outside of, the rotatable shaft 646. Similarly, FIG. 6 shows the drive-unit interface 656 disposed along the drive-unit connector 636 within the rotatable shaft 646. It will be understood that the drive-unit conductor interface 656, likewise, can be disposed at any suitable location along the drive-unit connector 636, either within, or outside of, the rotatable shaft 646.

In at least some embodiments, the adaptor 420 includes multiple catheter conductor interfaces 652. When the adaptor includes multiple catheter conductor interfaces 652, the catheter conductor interfaces 652 may be all within the rotatable shaft 646, or external to the rotatable shaft 646, or a combination of both. Similarly, in at least some embodiments the adaptor 420 includes multiple drive-unit conductor interfaces 656. When the adaptor includes multiple drive-unit conductor interfaces 656, the drive-unit conductor interfaces 656 may be all within the rotatable shaft 646, or external to the rotatable shaft 646, or a combination of both.

At least one adaptor conductor 662 extends along the adaptor 420 and electrically couples the catheter conductor interface(s) 652 to the drive-unit conductor interface(s) 656. In FIG. 6, the adaptor conductor 662 is shown extending through the rotatable shaft 646. In other embodiments, the adaptor conductor 662 is disposed in the housing 622 external to the rotatable shaft 646. In at least some embodiments, a first portion of the adaptor conductor 662 is disposed in the rotatable shaft 646 and a second portion of the adaptor conductor 662 is disposed in the housing 622 and external to the rotatable shaft 646.

One or more tuning elements 666 are electrically coupled to the at least one adaptor conductor 662. The tuning elements 666 can be disposed at any suitable location within the housing 622. In at least some embodiments, the one or more tuning elements 666 are at least partially disposed within the rotatable shaft 646. In at least some embodiments, the one or more tuning elements 666 are entirely disposed within the rotatable shaft 646.

The tuning element(s) 666 are configured to adjust electrical signals propagating along the at least one adaptor conductor 662 between the drive unit 410 and the catheter 402 to enhance performance of the IVUS imaging system. The tuning element can enhance performance of the IVUS system in any number of different ways including, for example, improving imaging quality, improving sensitivity, reducing noise, reducing emissions, or the like or combinations thereof.

The tuning element(s) 666 may include one or more tuning circuits, or filters, formed from capacitors, inductors, and the like. For example, an LC circuit can be used as, or as a part of, a tuning element. The tuning element(s) may include other elements for enhancing performance of the IVUS imaging system including, for example, one or more common mode chokes tuned to a specific transducer frequency, or range of frequencies.

In at least some embodiments, the tuning element 666 is configured to adjust electrical signals propagating along the at least one adaptor conductor 662 based, at least in part, on an operational frequency of the at least one transducer (312 in FIG. 3) disposed in the catheter. In at least some embodiments, a particular adaptor is configured to operate with catheters having a particular operational frequency, or with catheters having operational frequencies that are within a particular range of frequencies.

Operational frequencies for catheters can vary, depending on various factors and desired uses. As mentioned above, operational frequencies of catheters of IVUS imaging systems are typically in the range of 5 MHz to 60 MHz. For example, an IVUS imaging system may include multiple different catheters, such as a first catheter having an operational frequency of 60 MHz, a second catheter having an operational frequency of 40 MHz, a third catheter having an operational frequency of 30 MHz, a fourth catheter having an operational frequency of 15 MHz, and a fifth catheter having an operational frequency of 9 MHz. A medical practitioner may select one of these different catheters for a particular procedure and use the same drive unit with the catheter, regardless of the operational frequency of the selected catheter.

In at least some embodiments, an adaptor is selected to enhance performance of the IVUS imaging system based on the operating frequency of the selected catheter. The selection of which adaptor to use may be based on the particular frequency, or range of frequencies, of the one or more tuning elements of the adaptor.

For example, in one embodiment a first adaptor is configured to enhance performance of IVUS systems having catheters with an operational frequency of 60 MHz, while a second adaptor is configured to enhance performance of IVUS systems having catheters with an operational frequency of 40 MHz, while a third adaptor is configured to enhance performance of IVUS systems having catheters with operational frequency of 30 MHz, while a fourth adaptor is configured to enhance performance of IVUS systems having catheters with an operational frequency of 15 MHz, while a fifth adaptor is configured to enhance performance of IVUS systems having catheters with an operational frequency of 9 MHz. Accordingly, using the above example, a user may select the first adaptor for use with the first catheter, the second adaptor for use with the second catheter, the third adaptor for use with the third catheter, the fourth adaptor for use with the fourth catheter, the fifth adaptor for use with the fifth catheter.

In some embodiments, the one or more tuning elements of a particular adaptor can be adapted for particular frequency ranges that include one or more of the above-mentioned operational frequencies. For example, in at least some embodiments, a first adaptor is configured to enhance performance of IVUS systems having catheters with operational frequencies that are greater than 5 MHz and less than 65 MHz, or greater than 5 MHz and less than 45 MHz, or greater than 5 MHz and less than 35 MHz, or greater than 5 MHz and less than 20 MHz, or greater than 5 MHz and less than 15 MHz, or greater than 10 MHz and less than 65 MHz, or greater than 10 MHz and less than 45 MHz, or greater than 10 MHz and less than 35 MHz, or greater than 10 MHz and less than 20 MHz, or greater than 25 MHz and less than 65 MHz, or greater than 25 MHz and less than 45 MHz, or greater than 25 MHz and less than 35 MHz, or greater than 35 MHz and less than 65 MHz, or greater than 35 MHz and less than 45 MHz. Accordingly, a user may select the first adaptor for use with any number of different catheters having operational frequencies that fall within the operational range of frequencies of the tuning element(s).

Figure 9:
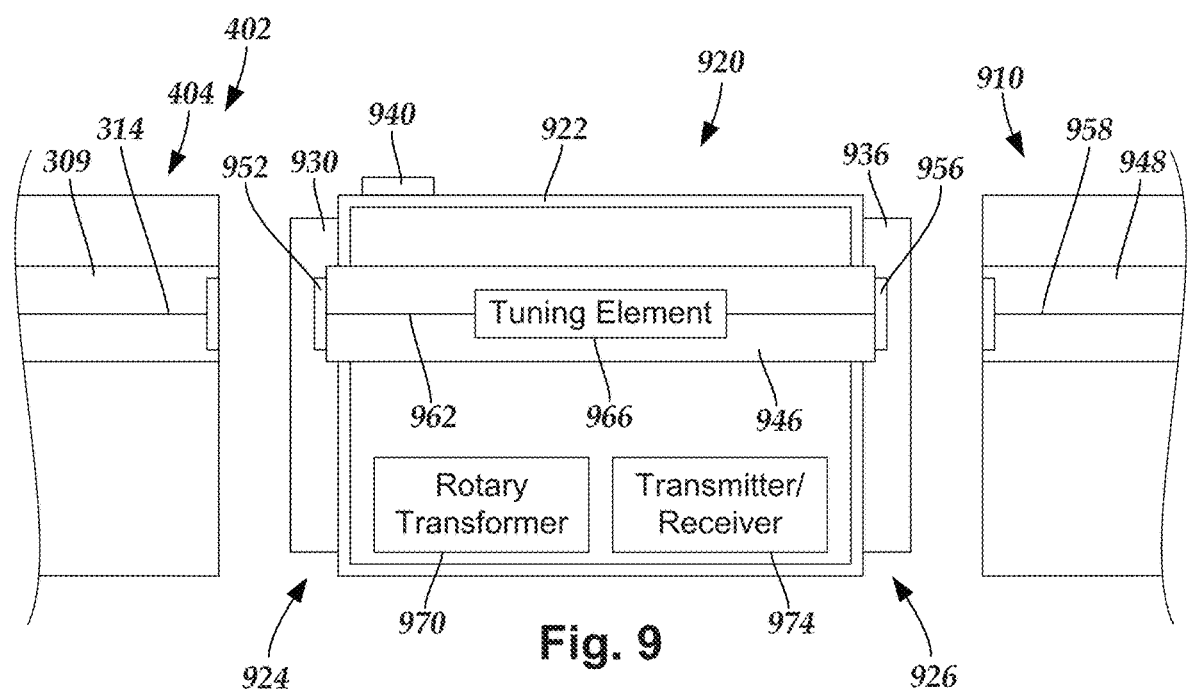
FIG. 9 is a schematic side view of another embodiment of an adaptor disposed between the catheter of FIG. 4 and a drive unit, according to the invention.

Turning to FIG. 9, the adaptor 420 described above, with reference to FIGS. 6-8, is configured to operate with a fully-functional drive unit. In which case, the catheter and drive unit can be directly coupled together and operated without using the adaptor. In at least some embodiments, the adaptor is configured for use with a drive unit that lacks one or more components necessary for functionality, thereby rendering the drive unit non-functional when coupled directly to a catheter. In at least some embodiments, the one or more components lacking in the drive unit, and necessary for functionality of the drive unit, are instead disposed in the adaptor. In which case, the drive unit becomes functional when coupled to the adaptor. It may be advantageous to form the IVUS system to incorporate one or more drive unit elements into the adaptor to increase the tunability of the adaptor and, therefore, to potentially further enhance performance of the IVUS system, as compared to the adaptor described above with reference to FIGS. 6-8.

As mentioned above, the drive unit may include components (e.g., a transmitter, receiver, rotary transformer, and the like) along the signal path that may be insufficient to operate consistently across a wide range of catheter frequencies (e.g., 9 MHz to 60 MHz). These components can be adapted to increase performance of the imaging system at particular frequencies, or ranges of frequencies. As described herein, one or more of the components conventionally disposed in the drive unit (e.g., a transmitter, receiver, rotary transformer, and the like) can be removed from the drive unit and, instead, disposed in the adaptor. In which case, those components (e.g., a transmitter, receiver, rotary transformer, and the like) can be tailored to a particular frequency, or frequency range, to accommodate a particular catheter, or group of catheters.

In at least some embodiments, the adaptor is tuned for the same center frequency as the catheter with which it would be used and would have as flat response as reasonably possible over a frequency range around the center frequency. For example, for a 60 MHz catheter, the drive unit with an adaptor may have flat response from 40 MHz to 80 MHz as a minimum. The tunable components within the adaptor may include, for example, the transmitter, receiver, rotary transformer, isolation transformers, common mode choke, and tuning circuits. Higher frequency and wider bandwidth transducers may be implemented in the future, so an adaptor may, for example, have a center frequency of 80 MHz and flat response from 40 MHz to 120 MHz.

Figure 10A:
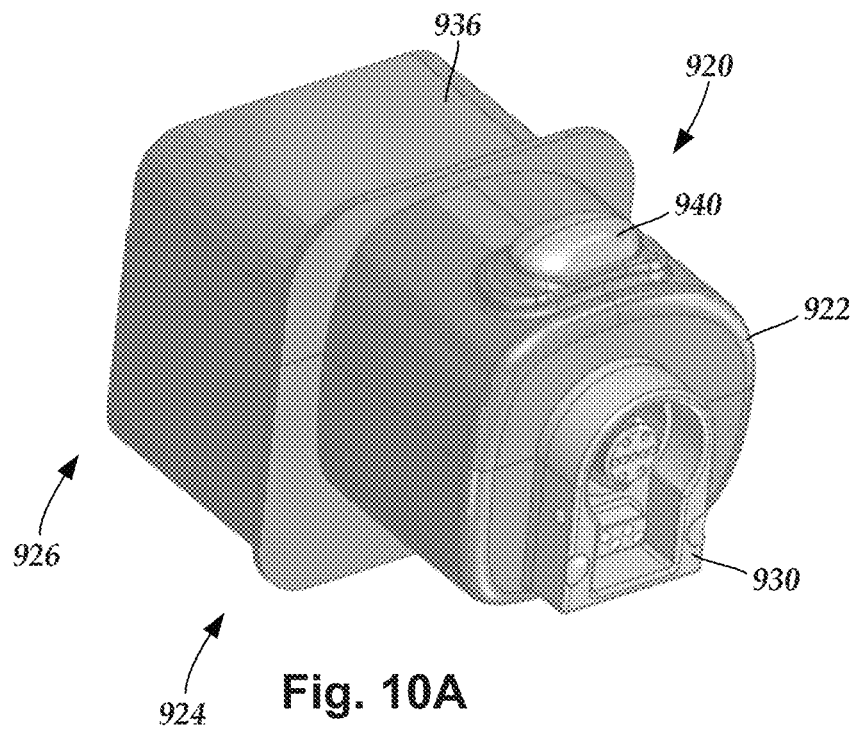
FIG. 10A is a schematic perspective view of one embodiment of the adaptor of FIG. 9 suitable for coupling the catheter of FIG. 4 to the drive unit of FIG. 9, according to the invention.
Figure 10B:
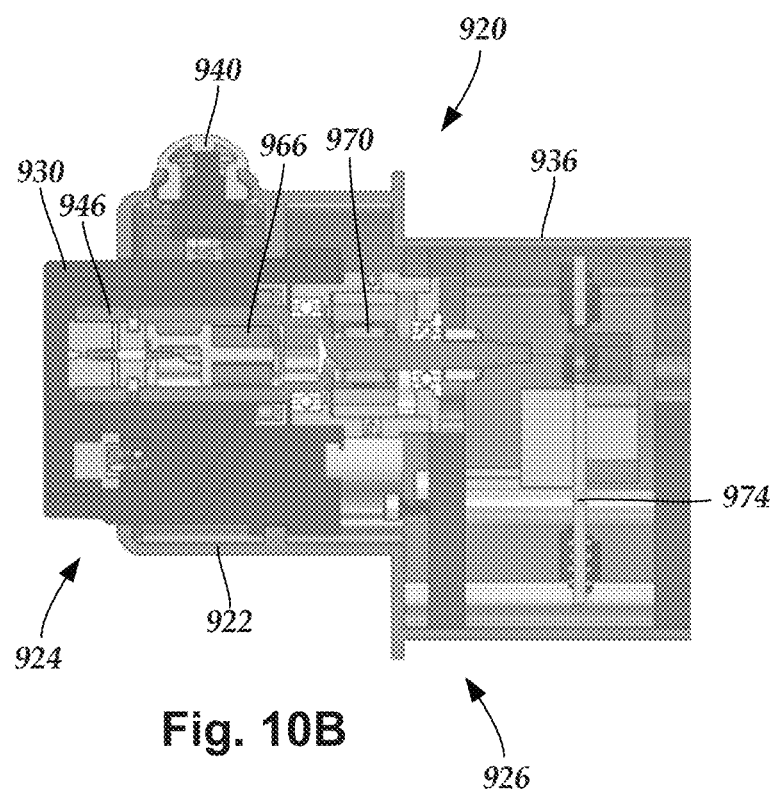
FIG. 10B is a schematic cross-sectional view of one embodiment of the adaptor of FIG. 10A, according to the invention.

FIG. 9 shows, in schematic side view, another embodiment of an adaptor 920 suitable for coupling the catheter, such as the catheter 402, to another embodiment of a drive unit 910. FIG. 10A shows one embodiment of the adaptor 920 in perspective view. FIG. 10B shows the adaptor 920 in cross-sectional view. In at least some embodiments, the adaptor is reusable.

The adaptor 920 includes a housing 922 having a first end 924 and a second end 926. In at least some embodiments, the second end 926 is opposite to the first end 924. A catheter connector 930 is disposed along the first end 924 of the housing 922 and is configured for receiving a catheter hub, such as the catheter hub 404. In at least some embodiments, the catheter connector 930 is similar to a catheter-receiving connector of a conventional drive unit. In at least some embodiments, the catheter connector 930 is configured for receiving a catheter hub by plugging the catheter into the catheter connector 930.

A drive-unit connector 936 is disposed along the second end 926 of the housing 922 and is configured for coupling the adaptor 920 to the drive unit 910. In at least some embodiments, the drive-unit connector 636 is similar to a drive-unit-receiving connector of a conventional catheter hub. In at least some embodiments, the drive-unit connector 936 plugs into the drive unit 910.

In FIG. 9, the catheter connector 930 and the drive-unit connector 936 are both shown extending outwardly from the housing 922, for clarity of illustration. In at least some embodiments, at least a portion of at least one of the catheter connector 939 or the drive-unit connector 936 extends inwardly with respect to the housing 922.

An optional catheter release 940 is disposed along the housing 922. The catheter release 940 controls release of the catheter 402 from the adaptor 920 when the catheter 402 is coupled to the adaptor 920. In at least some embodiments, once the catheter 402 is received by the adaptor 920, the catheter 402 remains retained by the adaptor 920 until the catheter release 940 is activated to enable the catheter 402 to be removed from the adaptor 920. In at least some embodiments, the catheter release 940 is configured to enable a user to manually separate the catheter 402 from the adaptor 920 when the catheter is received by the catheter connector 930.

The adaptor 920 includes a rotatable shaft 946 disposed in the housing 922. The rotatable shaft 946 is suitable for transferring rotation generated by the drive unit 910 (e.g., by a drive-unit driveshaft 948) to the drive cable or driveshaft 309 of the catheter 402. In at least some embodiments, the rotatable shaft 946 extends from the catheter connector 930 to a drive-shaft coupler disposed along, or in proximity to, the second end 926 of the housing 922.

The adaptor 920 also is configured to enable an electrical signal path to extend between the drive unit and the catheter. The adaptor 920 includes a catheter conductor interface 952 disposed along the first end 924 of the housing 922 and configured to electrically couple to at least one transducer conductor 309 extending along the catheter 402. Similarly, a drive-unit conductor interface 956 is disposed along the second end 926 of the housing 922 and is configured to electrically couple to at least one electrical conductor 958 of the drive unit 910. The catheter conductor interface 952, or the drive-unit conductor interface 956, or both, can be formed in any suitable manner, such as pin headers.

In FIG. 6, the catheter conductor interface 952 is shown disposed along the catheter connector 930 within the rotatable shaft 946. It will be understood that the catheter conductor interface 952 can be disposed at any suitable location along the catheter connector 930, either within, or outside of, the rotatable shaft 946. Similarly, FIG. 9 shows the drive-unit interface 956 disposed along the drive-unit connector 936 within the rotatable shaft 946. It will be understood that the drive-unit conductor interface 956, likewise, can be disposed at any suitable location along the drive-unit connector 936, either within, or outside of, the rotatable shaft 946.

In at least some embodiments, the adaptor includes multiple catheter conductor interfaces 952. When the adaptor includes multiple catheter conductor interfaces 952, the catheter conductor interfaces 952 may be all within the rotatable shaft 946, or external to the rotatable shaft 946, or a combination of both. Similarly, in at least some embodiments the adaptor includes multiple drive-unit conductor interfaces 956. When the adaptor includes multiple drive-unit conductor interfaces 956, the drive-unit conductor interfaces 956 may be all within the rotatable shaft 946, or external to the rotatable shaft 946, or a combination of both.

At least one adaptor conductor 962 extends along the adaptor 920 and electrically couples the catheter conductor interface 952 to the drive-unit conductor interface 956. In FIG. 9, the adaptor conductor 962 is shown extending through the rotatable shaft 946. In other embodiments, the adaptor conductor 962 is disposed in the housing 922 external to the rotatable shaft 946. In at least some embodiments, a first portion of the adaptor conductor 962 is disposed in the rotatable shaft 946 and a second portion of the adaptor conductor 962 is disposed in the housing 922 and external to the rotatable shaft 946.

One or more tuning elements 966 are electrically coupled to the at least one adaptor conductor 962. The tuning elements 966 can be disposed at any suitable location within the housing 922. In at least some embodiments, the one or more tuning elements 966 are at least partially disposed within the rotatable shaft 946. In at least some embodiments, the one or more tuning elements 966 are entirely disposed within the rotatable shaft 946.

The tuning element(s) 966 are configured to adjust electrical signals propagating along the at least one adaptor conductor 962 between the drive unit 910 and the catheter 402 to enhance performance of the IVUS imaging system. The tuning element can enhance performance of the IVUS system in any number of different ways including, for example, improving imaging quality, improving sensitivity, reducing noise, reducing emissions, or the like or combinations thereof.

The tuning element(s) 966 may include one or more tuning circuits, or filters, formed from capacitors, inductors, and the like. The tuning element(s) may include other elements for enhancing performance of the IVUS imaging system including, for example, one or more common mode chokes.

In at least some embodiments, the tuning element 966 is configured to adjust electrical signals propagating along the at least one adaptor conductor 962 based, at least in part, on an operational frequency of the at least one transducer (312 in FIG. 3) disposed in the catheter. In at least some embodiments, a particular adaptor is configured to operate with catheters having a particular operational frequency, or with catheters having operational frequencies that are within a particular range of frequencies.

In at least some embodiments, the one or more tuning elements 966 are configured to match, or nearly match, the electrical impedance of the one or more transducer conductors 314 to the one or more transducers 312 over at least a subset of the operational frequency bandwidth of the one or more transducers 312. In at least some embodiments, matching, or nearly matching, the electrical impedance of the one or more transducer conductors 314 to the one or more transducers 312 over at least a subset of the frequency bandwidth of the one or more transducers 312 may improve the efficiency of signal propagation along the one or more transducer conductors 314, thereby potentially enhancing performance of the IVUS imaging system.

Operational frequencies for catheters can vary, depending on various factors and desired uses. As mentioned above, operational frequencies of catheters of IVUS imaging systems are typically in the range of 5 MHz to 60 MHz. For example, an IVUS imaging system may include multiple different catheters, such as a first catheter having an operational frequency of 60 MHz, a second catheter having an operational frequency of 40 MHz, a third catheter having an operational frequency of 30 MHz, a fourth catheter having an operational frequency of 15 MHz, and a fifth catheter having an operational frequency of 9 MHz. A medical practitioner may select one of these different catheters for a particular procedure and use the same drive unit with the catheter, regardless of the operational frequency of the selected catheter.

In at least some embodiments, an adaptor is selected to enhance performance of the IVUS imaging system based on the operating frequency of the selected catheter. The selection of which adaptor to use may be based on the particular frequency, or range of frequencies, of the one or more tuning elements of the adaptor.

For example, in one embodiment a first adaptor is configured to enhance performance of IVUS systems having catheters with an operational frequency of 60 MHz, while a second adaptor is configured to enhance performance of IVUS systems having catheters with an operational frequency of 40 MHz, while a third adaptor is configured to enhance performance of IVUS systems having catheters with operational frequency of 30 MHz, while a fourth adaptor is configured to enhance performance of IVUS systems having catheters with an operational frequency of 15 MHz, while a fifth adaptor is configured to enhance performance of IVUS systems having catheters with an operational frequency of 9 MHz. Accordingly, using the above example, a user may select the first adaptor for use with the first catheter, the second adaptor for use with the second catheter, the third adaptor for use with the third catheter, the fourth adaptor for use with the fourth catheter, the fifth adaptor for use with the fifth catheter.

In some embodiments, the one or more tuning elements of a particular adaptor can be adapted for particular frequency ranges that include one or more of the above-mentioned operational frequencies. For example, in at least some embodiments, a first adaptor is configured to enhance performance of IVUS systems having catheters with operational frequencies that are greater than 5 MHz and less than 65 MHz, or greater than 5 MHz and less than 45 MHz, or greater than 5 MHz and less than 35 MHz, or greater than 5 MHz and less than 20 MHz, or greater than 5 MHz and less than 15 MHz, or greater than 10 MHz and less than 65 MHz, or greater than 10 MHz and less than 45 MHz, or greater than 10 MHz and less than 35 MHz, or greater than 10 MHz and less than 20 MHz, or greater than 25 MHz and less than 65 MHz, or greater than 25 MHz and less than 45 MHz, or greater than 25 MHz and less than 35 MHz, or greater than 35 MHz and less than 65 MHz, or greater than 35 MHz and less than 45 MHz. Accordingly, a user may select the first adaptor for use with any number of different catheters having operational frequencies that fall within the operational range of frequencies of the tuning element(s).

As mentioned above, the embodiment of the adaptor 920 described above, with respect to FIGS. 9-10B, includes one or more essential elements of the drive unit that, when disposed in the adaptor instead of the drive unit, can be adapted (e.g., tuned), based on an operational frequency of the catheter, to improve performance of an IVUS imaging system. In at least some embodiments, moving one or more essential, tunable elements the drive unit to the adaptor enables the drive unit to remain generic to a wide range of catheters with different operational frequencies, while the adaptor 920 can be selected based on a specific operational frequency, or range of operational frequencies.

In at least some embodiments, a rotary transformer 970 is disposed in the housing 922 of the adaptor 920. The rotary transformer 970 is configured to couple electrical signals between components that rotate relative to one another, such as between a rotating driveshaft and stationary electronics. Disposing the rotary transformer 970 on the adaptor 920, instead of in the drive unit 910, may enable the bandwidth of the rotary transformer 970 to be adapted to better match the operational frequency of the catheter than were the rotary transformer to be disposed in the drive unit, where it would typically be formed to operate over a wider range of operational frequencies than may be needed given the operation frequency of the catheter.

In at least some embodiments, a transmitter/receiver 974 is disposed in the housing 922 of the adaptor 920. The transmitter/receiver 974 generates/receives electric pulses that may be input to/received from the transducers(s). Disposing the transmitter/receiver 974 on the adaptor 920, instead of in the drive unit 910, may enable transmitter/receiver 974 to be adapted to better match the operational frequency of the catheter than were the transmitter/receiver to be disposed in the drive unit, where it would typically be formed to operate over a wider range of operational frequencies than may be needed given the operation frequency of the catheter.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An adaptor for adjusting electrical signals propagated along an electrically conductive path between a drive unit and a catheter of an intravascular ultrasound imaging system, the adaptor comprising:
 a housing having a first end and a second end;
 a catheter connector disposed along the first end of the housing, the catheter connector configured and arranged to receive the catheter, to receive a proximal end of a drive cable disposed within the catheter, and to releasably secure a proximal end of the catheter and the proximal end of the drive cable to the housing;
 a drive-unit connector disposed along the second end of the housing, the drive-unit connector configured and arranged to couple the adaptor to the drive unit and to releasably secure the drive unit to the housing;
 a catheter conductor interface disposed along the first end of the housing and configured and arranged to electrically couple to at least one transducer conductor extending along the catheter;
 a drive-unit conductor interface disposed along the second end of the housing and configured and arranged to electrically couple to at least one electrical conductor of the drive unit;
 at least one adaptor conductor electrically coupling the catheter conductor interface to the drive-unit conductor interface;
 a catheter release disposed along the housing, the catheter release configured and arranged to enable a user to manually separate the catheter from the adaptor when the catheter is received by the catheter connector; and
 at least one tuning element electrically coupled to the at least one adaptor conductor, the at least one tuning element configured and arranged to adjust electrical signals propagating along the at least one adaptor conductor based, at least in part, on an operational frequency of at least one transducer disposed in the catheter.

2. The adaptor of claim 1, further comprising a rotatable shaft disposed in the housing and extending from the catheter connector to the drive-unit connector, the rotatable shaft configured and arranged to transfer rotational motion generated within the drive unit to the drive cable when the catheter is received by the catheter connector and the adaptor is coupled to the drive unit.

3. The adaptor of claim 2, wherein the at least one tuning element is disposed entirely within the rotatable shaft.

4. The adaptor of claim 2, further comprising a rotary transformer disposed in the housing.

5. The adaptor of claim 1, further comprising a transmitter, a receiver, or both a transmitter and a receiver disposed in the housing.

6. The adaptor of claim 1, wherein the at least one tuning element comprises at least one filter.

7. The adaptor of claim 1, wherein the at least one tuning element comprises at least one tuning circuit.

8. The adaptor of claim 1, wherein the at least one tuning element is configured and arranged to adjust signals propagated along the at least one adaptor conductor to reduce noise in images generated from the intravascular ultrasound imaging system.

9. The adaptor of claim 1, wherein the at least one tuning element is configured and arranged to adjust electrical signals propagating along the at least one adaptor conductor when those electrical signals correspond to an operational frequency of the at least one transducer of the catheter that is within a first frequency range.

10. The adaptor of claim 9, wherein the first frequency range is no less than 5 MHz and no greater than 65 MHz.

11. The adaptor of claim 9, wherein the first frequency range is no less than 5 MHz and no greater than 35 MHz.

12. The adaptor of claim 9, wherein the first frequency range is no less than 35 MHz and no greater than 65 MHz.

13. An adaptor for adjusting electrical signals propagated along an electrically conductive path between a drive unit and a catheter of an intravascular ultrasound imaging system, the adaptor comprising:
 a housing having a first end and a second end;
 a catheter connector disposed along the first end of the housing, the catheter connector configured and arranged to receive the catheter;
 a drive-unit connector disposed along the second end of the housing, the drive-unit connector configured and arranged to secure the second end of the housing to to the drive unit;
 a catheter conductor interface disposed along the first end of the housing and configured and arranged to electrically couple to at least one transducer conductor extending along the catheter;
 a drive-unit conductor interface disposed along the second end of the housing and configured and arranged to electrically couple to at least one electrical conductor of the drive unit;
 a catheter release disposed along the housing, the catheter release configured and arranged to enable a user to manually separate the catheter from the adaptor when the catheter is received by the catheter connector;
 at least one adaptor conductor electrically coupling the catheter conductor interface to the drive-unit conductor interface; and
 at least one tuning element electrically coupled to the at least one adaptor conductor, the at least one tuning element configured and arranged to adjust electrical signals propagating along the at least one adaptor conductor based, at least in part, on an operational frequency of at least one transducer disposed in the catheter;
 wherein the at least one tuning element comprises at least one common mode choke.

14. A catheter assembly for an intravascular ultrasound system, the catheter assembly comprising:
 a catheter having a longitudinal length, a distal portion, and a proximal end, the catheter defining a lumen extending along at least a portion of the catheter;
 an imaging device housing disposed in the lumen along the distal portion of the catheter;
 a drive shaft extending from the imaging device housing, the drive shaft having a proximal end disposed adjacent to the proximal end of the catheter;
 at least one ultrasound transducer disposed in the imaging device housing, the at least one ultrasound transducer configured and arranged to transform applied electrical signals to acoustic signals within a frequency bandwidth centered at an operational frequency, transmit the acoustic signals, receive corresponding echo signals, and transform the received echo signals to electrical signals;
 at least one transducer conductor electrically coupled to the at least one transducer and in electrical communication with the proximal end of the catheter;

an adaptor directly attached to the proximal end of the catheter, the proximal end of the drive shaft, and a drive unit; and a catheter release disposed along the adapter, the catheter release configured and arranged to enable a user to manually separate the catheter from the adaptor.

15. The catheter assembly of claim 14, wherein the adapter comprises:

a housing having a first end and a second end;

a catheter connector disposed along the first end of the housing, the catheter connector being configured to be secured to a proximal end of the catheter;

a drive-unit connector disposed along the second end of the housing, the drive-unit connector being configured to be secured to the drive unit;

a catheter conductor interface disposed along the first end of the housing and configured and arranged to electrically couple to at least one transducer conductor extending along the catheter;

a drive-unit conductor interface disposed along the second end of the housing and configured and arranged to electrically couple to at least one electrical conductor of the drive unit;

the catheter release disposed along the housing, the catheter release configured and arranged to enable the user to manually separate the catheter from the adaptor when the catheter is received by the catheter connector;

at least one adaptor conductor electrically coupling the catheter conductor interface to the drive-unit conductor interface; and at least one tuning element electrically coupled to the at least one adaptor conductor, the at least one tuning element configured and arranged to adjust electrical signals propagating along the at least one adaptor conductor based, at least in part, on an operational frequency of at least one transducer disposed in the catheter.

* * * * *